(12) United States Patent
Noumeir

(10) Patent No.: US 8,458,202 B2
(45) Date of Patent: Jun. 4, 2013

(54) METHODS AND SYSTEMS FOR CONSOLIDATING MEDICAL INFORMATION

(76) Inventor: Rita Noumeir, Saint Laurent (CA)

( * ) Notice: Subject to any disclaimer, the term of this patent is extended or adjusted under 35 U.S.C. 154(b) by 695 days.

(21) Appl. No.: 12/300,244

(22) PCT Filed: Jun. 8, 2007

(86) PCT No.: PCT/IB2007/004357
§ 371 (c)(1),
(2), (4) Date: Nov. 10, 2008

(87) PCT Pub. No.: WO2008/084330
PCT Pub. Date: Jul. 17, 2008

(65) Prior Publication Data
US 2009/0164474 A1 Jun. 25, 2009

Related U.S. Application Data

(60) Provisional application No. 60/811,888, filed on Jun. 8, 2006.

(51) Int. Cl.
*G06F 17/30* (2006.01)

(52) U.S. Cl.
USPC .......................................... 707/756

(58) Field of Classification Search
CPC ............................. G06F 19/321; G06Q 50/22
USPC ........................................ 707/741, 756, 804
See application file for complete search history.

(56) References Cited

U.S. PATENT DOCUMENTS

| 6,260,021 | B1 * | 7/2001 | Wong et al. ....................... 705/2 |
| 6,718,409 | B2 | 4/2004 | Houlberg |
| 6,766,375 | B2 | 7/2004 | Hadland |
| 6,987,560 | B2 | 1/2006 | Morgan et al. |
| 7,028,182 | B1 | 4/2006 | Killcommons |
| 7,606,861 | B2 * | 10/2009 | Killcommons et al. ...... 709/206 |
| 2004/0176667 | A1 * | 9/2004 | Mihai et al. ................... 600/300 |
| 2006/0004745 | A1 * | 1/2006 | Kuhn et al. ....................... 707/4 |
| 2007/0061393 | A1 * | 3/2007 | Moore .......................... 709/201 |
| 2009/0132285 | A1 * | 5/2009 | Jakobovits ....................... 705/3 |
| 2009/0319291 | A1 * | 12/2009 | Noordvyk et al. ................ 705/2 |

FOREIGN PATENT DOCUMENTS

WO      2005119443  A2      12/2005

OTHER PUBLICATIONS

JP Publication No. JP7320034(A), published Dec. 8, 2995. Applicant: Toshiba Medical Eng. (abstract only).
International Search Report dtd. Jul. 17, 2009 for PCT/IB07/004357. Applicant: Softmedical, Inc.

* cited by examiner

*Primary Examiner* — Jorge A Casanova
(74) *Attorney, Agent, or Firm* — Burns & Levinson LLP; Orlando Lopez

(57) ABSTRACT

Methods and systems for enabling data communication from an image archiving system and a data storage/index/retrieving system.

40 Claims, 8 Drawing Sheets

FIG. 7

RECEIVING/TRANSMITTING DATA FROM/TO THE GROUP OF IMAGE REPORTING/ ARCHIVING SYSTEMS TO/FROM A SYSTEM FOR CONVERTING DATA
460

RETRIEVING DATA FROM THE GROUP OF IMAGE REPORTING/ARCHIVING SYSTEMS AND THE DATA STORAGE/INDEX/RETRIEVING SYSTEM
465

RECEIVING/TRANSMITTING DATA FROM/TO THE DATA STORAGE/INDEX/RETRIEVING SYSTEM TO/FROM THE SYSTEM FOR CONVERTING DATA
470

CONVERTING DATA FROM ONE SYSTEM FROM THE GROUP OF IMAGE REPORTING/ ARCHIVING SYSTEMS AND THE DATA STORAGE/INDEX/RETRIEVING SYSTEM INTO DATA FOR ANOTHER DIFFERENT SYSTEM FROM THE GROUP OF IMAGE REPORTING/ ARCHIVING SYSTEMS AND THE DATA STORAGE/INDEX/RETRIEVING SYSTEM
475

METHODS AND SYSTEMS FOR CONSOLIDATING MEDICAL INFORMATION

CROSS REFERENCE TO RELATED APPLICATIONS

This application claims priority of U.S. Provisional Patent Application Ser. No. 60/811,888, METHODS AND SYSTEMS FOR CONSOLIDATING MEDICAL INFORMATION, filed on Jun. 8, 2006, which is incorporated by reference herein.

BACKGROUND

A variety of different systems are utilized in a healthcare environment to store, organize and retrieve different types of medical or patient related information. Typical systems are described below.

In a healthcare environment, a Picture Archiving and Communication System (PACS) concerns the archiving, communication and visualization of medical imaging and other related information, as well as with the workflow management for the generation and interpretation of such information. PACS designates the overall system composed of archives, visualization stations, image digitizers, and communication interfaces.

The expression "imaging information object" will be used to designate an image, an information object related to an image, or a set of related images and/or information objects. PACS also relates to with the problem of how to transfer imaging information objects between two systems, a source system and a destination. Generally, PACS includes a system, designated with the term "archive", that is composed of: a storage media that stores the data of the imaging information objects, a database that stores the attributes of imaging information objects in order to retrieve their data from the storage media as a response for a query, and an interface software for communicating with peers according to a standard communication protocol.

A system, a peer within the PACS, is composed of an interface software for communicating with peers according to a standard communication protocol and a imaging information object consumer that acts on that imaging information object's data. The destination system can be for example, an archive, a printer capable of printing the data of the imaging information object on papers or films, or a viewer capable of displaying the data of the imaging information object on monitors. The source and the destination systems can be hosted by two distinct computers connected to a network or by the same computer. In the later case, the communication interface software is not necessary. The most widely used standard for communicating medical images over a network is the Digital Imaging and Communications in Medicine (DICOM) standard that has been developed by the American College of Radiology (ACR) and the National Electrical Manufacturers Association (NEMA).

FIG. 2 illustrates the image flow in PACS systems. The images are acquired by modalities, digitized if necessary, and communicated through the communication interface to the archive and one or multiple visualization stations according to a pre-configured image flow. The visualization station receives the images and stores them on a local short-term storage media. A "pre-fetch" software triggers the transfer of scheduled patients' old images, from the archive to one or multiple visualization station according to a pre-configured image flow.

PACS manages imaging information objects that are generated, visualized and interpreted in an imaging department as depicted in FIG. 3. The business of the imaging department is to deliver an imaging result to a customer who is the recipient or beneficiary of the result. The imaging process is initiated by a request for an imaging procedure for a specific patient. The imaging process result is an imaging report that is a document whose content holds the interpretation and the impressions of the radiologist. The imaging process customer, the recipient of the imaging report, is a healthcare specialist that is usually outside of the imaging department, and is involved in the patient care. To achieve one complete imaging process, from ordering to result generation, multiple steps are usually performed. These include scheduling of acquisition, image acquisition, image processing, image interpretation, report recording, report transcription and report verification. Each step may be performed by a different system. For example, a Radiology Information System (RIS) may manage scheduling of acquisition, report recording, report transcription and report verification. The PACS on the other hand, manages image visualization to enable image interpretation.

Of particular interest herein the imaging information objects generated during an imaging service, for a specific patient. These imaging information objects include images and other related information in addition to the imaging report. These imaging information objects constitute important patient's clinical and diagnostic information. Therefore they are archived for a long period and make up part of the patient's health history. They may be archived and managed by different systems. For example, images and related information are archived and managed by the PACS while the imaging report is archived and managed by the information system such as the RIS. Moreover, they are used as prior information in future patient's imaging processes. In fact, while performing an interpretation task, the imaging specialist compares current images with prior ones and consults prior reports. Therefore, it is very important for a specialist to access all relevant patient's history in order to provide optimal care.

Also, of particular interest herein is the patient identification that is used to link the imaging information objects to a specific real patient. This identification is encoded within each patient's information object. It is used by the managing system to identify all information objects that belong to a specific patient. When a system receives an information object using a communication protocol for example, it extracts the patient identification from that information object in order to internally link the object to that patient. Therefore, a system can identify, using the patient identification, all information objects belonging to a specific real patient.

Usually, systems that cooperate within the same enterprise use the same patient identification. This is achieved by sharing patient identification with messages exchanged on the network or manually. Moreover, a specific report is linked to the images via a single shared identification such as procedure identification or more commonly the order identification. Again, such identification is shared by the various systems with messages exchanged on the network or manually.

In many situations, a specific patient may have imaging information in different enterprises. An enterprise designates a hospital, a group of hospitals, an imaging center, or any institution involved in the patient care. Providing access to prior information while performing a diagnostic imaging service is necessary to ensure optimal care. Prior information may reside in a different enterprise. Prior information includes prior images. Prior images are needed to perform comparisons with newly acquired images. Prior information also includes prior reports. Prior reports are needed to access prior interpretations and results.

In addition to sharing patient information between multiple enterprises, it is important to share information from various clinical domains. Examples include access to laboratory results while performing an imaging interpretation task. Patient Electronic Health Record (EHR) designates one or multiple systems that cooperate together to provide access to the patient's health history. EHR usually provides functionalities such as query and retrieve information for a specific patient as well as publishing health information for a specific patient. (In providing the functionality of query and retrieve information, the EHR operates in a manner akin to a registry or a system having the functionality of an index/retrieve system.) Frameworks for sharing patient information between multiple enterprises and between various clinical domains are essential and central to the EHR. Of particular interest herein is that such frameworks use communication protocol and information object encoding formats that are different from those used within an imaging department. Therefore, deployed PACS cannot communicate with EHR as they cannot communicate with the EHR communication protocol. Furthermore, patient identification is not usually consistent between the imaging department and the EHR or other enterprises. Also, security requirements are commonly dissimilar when communicating information on the network between two systems that belong to the same imaging department or when communicating information on the network between a system that belongs to the imaging department and a system the does not belong to the imaging department. For example, information exchange may take place on an unsecured network within the imaging department while secure communication involving encryption or systems authentication may be needed while communicating with systems outside of the imaging department.

In the typical systems described above, it would be desirable to provide existing PACS the capability of bi-directional communication with the EHR for querying and retrieving information from other enterprises or other clinical domains as well as for submitting imaging information to the EHR.

It would also be desirable to provide existing PACS information retrieved from the EHR in a way that enables them to process the information and to integrate it within their data model and their persistence framework. This implies transforming the information into an encoding format that is acceptable for the PACS and ensuring that the information is identified with identifiers that are meaningful and consistent with those used by the PACS.

It would also be desirable to be able to communicate with various communication protocols satisfying different security requirements.

SUMMARY

Embodiments of methods and systems for enabling data communication from an image archiving system (in one exemplary embodiment, these teachings not be limited only to that embodiment, a system including a PACS and a Radiology Information System) and a data storage/index/retrieving system (in one exemplary embodiment, this teaching is not being limited only to that embodiment, an EHR system) are disclosed.

BRIEF DESCRIPTION OF THE DRAWINGS

For a better understanding of the present teachings, together with other and further needs thereof, reference is made to the accompanying drawings and detailed description and its scope will be pointed out in the appended claims.

FIG. 7 is a schematic flowchart representation of one embodiment of the method of these teachings;

DETAILED DESCRIPTION

Figure 5:
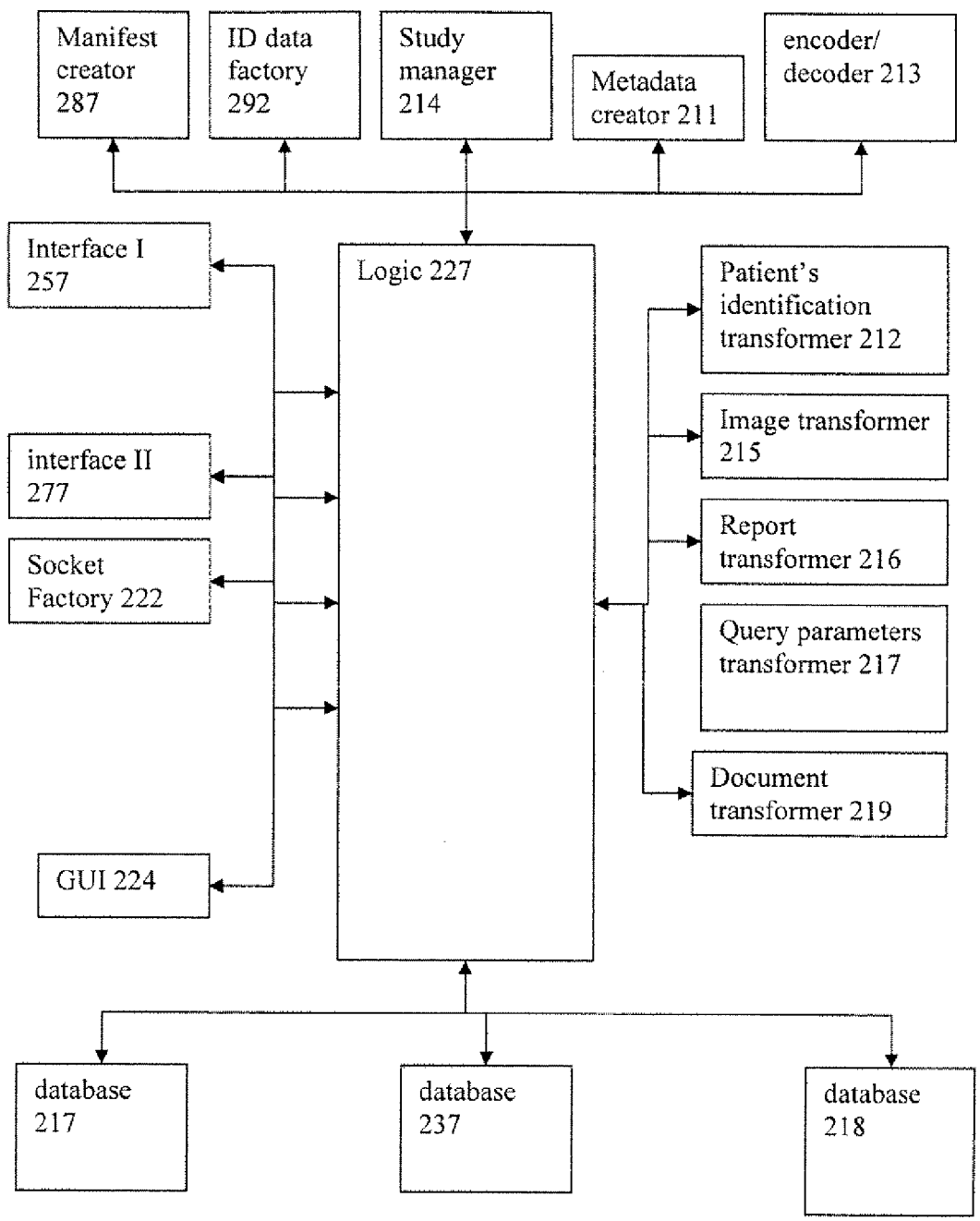
FIG. 5 is a schematic block diagram representation of one embodiment of the system of these teachings.

In one embodiment, shown in FIG. 5, the system of these teachings for enabling data communication from an image archiving system (in one exemplary embodiment, these teachings not be limited only to that embodiment, a system including a PACS and a Radiology Information System) and a data storage/index/retrieving system (in one exemplary embodiment, this teaching is not being limited only to that embodiment, an EHR system), includes an interface 257 capable of receiving/sending data according to a first protocol, the first protocol being utilized for data communication from the image archiving system, another interface 277 capable of receiving/sending data according to a second protocol, the second protocol being utilized for data communications (data as used herein includes both data and metadata) from the data storage/index/retrieving system, one or more data conversion subsystems 212, 215 capable of converting data from a format used by the image archiving system into data in a format utilized by the data storage/index/retrieving system, at least another data conversion subsystem 212, 216, 217 and 219 that converts data from a format used by the data storage/index/retrieving system into data in a format utilized by utilized by the image archiving system, at least one database 217, 237, 218 capable of storing addresses and data from data systems, the data systems including the image archiving system and the data storage/index/retrieving system, means for receiving/transmitting data from/to the data storage/index/retrieving system, means for receiving/transmitting data from/to the image archiving system, means for retrieving, from the at least one database, data from the image archiving system and the data storage/index/retrieving system and means for converting data from one of the image archiving system and the data storage/index/retrieving system into data for a different one of the image archiving system and the data storage/index/retrieving system (the means being embodied in the logic unit 227, the manifest creator 287, the ID data factory 292, the study manager 214, the metadata creator 211, the encoder/decoder 213, the socket factory 222 and the graphical user interface-GUI-224; "factory" as used herein refers to means to "manufacture" software object instances from a definition, usually a class definition; "socket" as used herein refers to interfaces and protocols for peer to peer or interprocess communication; "sockets" are exemplary means for defining communication endpoints).

Figure 6:
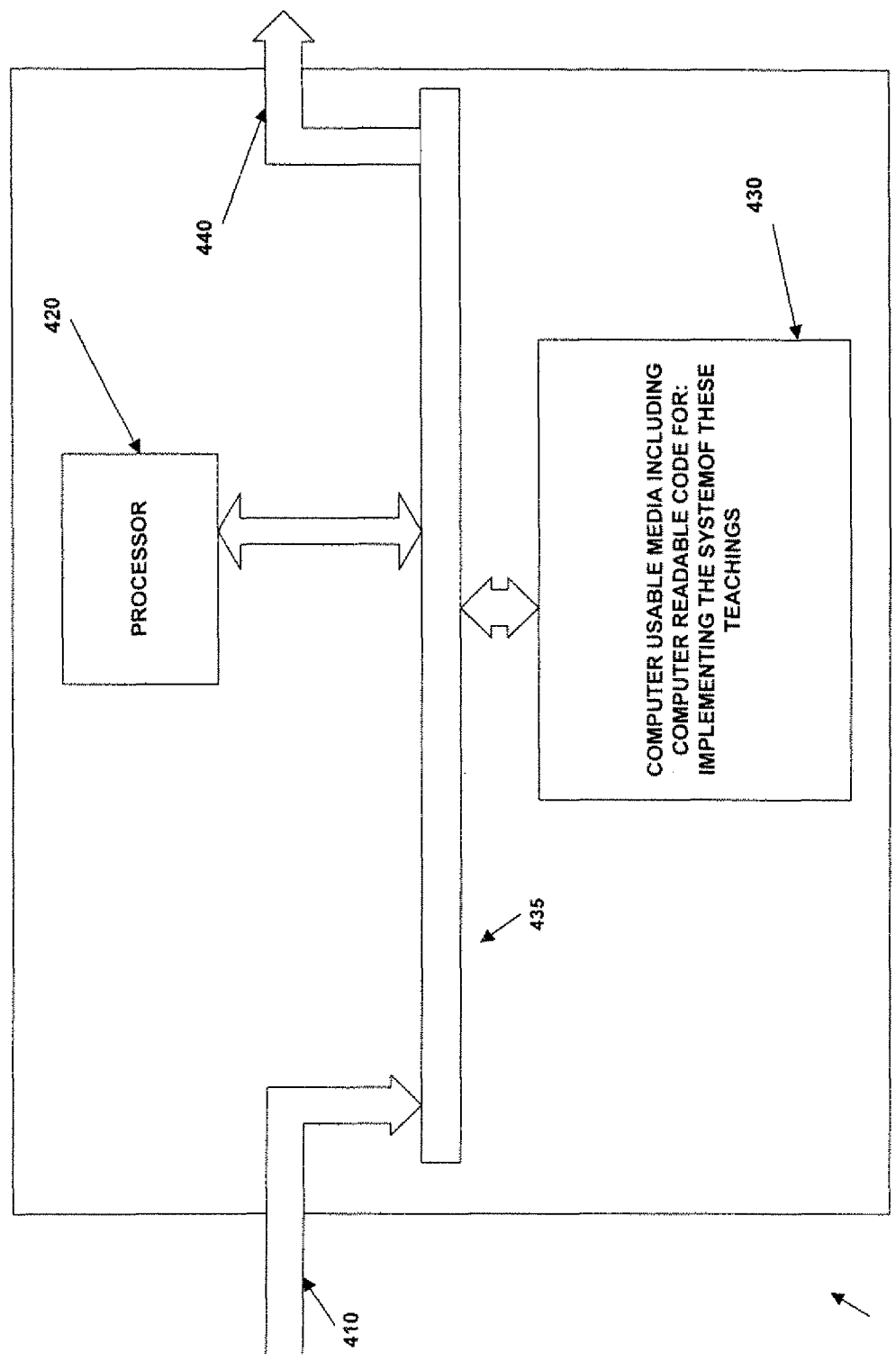
FIG. 6 is a schematic block diagram representation of a component of one embodiment of the system of these teachings.

Although the above stated means can be implemented by computer readable code, embodied in computer usable media 430, as shown in FIG. 6, where the computer readable code is capable of causing one or more processors 420 to perform the functions disclosed hereinabove (also shown in FIG. 6 are interconnection means 435, such as a computer bus, for operatively connecting the one or more processors 420 and the computer usable media 430, as well as input 410 connections and output 440 connections), other means are also within the scope of these teachings in which a combination of hardware and software or hardware alone is used to perform the functions (exemplary embodiments of hardware/software are field programmable devices and application-specific integrated circuits designed to embody the logic to perform the functions).

The above described embodiment of the system of these teachings can be placed in the network including a group of image reporting/archiving systems having an image archiving system, the image archiving system receiving/transmitting image data according to a first protocol and an image information system, the image information system receiving/transmitting image information data according to a second protocol, and a data storage/index/retrieving system; the data storage/index/retrieving system receiving/transmitting data according to a third protocol.

In one embodiment of the method of these teachings for communicating data between a group of image reporting/archiving systems and a data storage/index/retrieving system, shown in FIG. 7, data from/to the group of image reporting/archiving systems is received/transmitted to/from a system for converting data (step 460, FIG. 7), data for the group of image reporting/archiving systems and the data storage/index/retrieving system are retrieved (step 465, FIG. 7), data from one system from the group of image reporting/archiving systems and the data storage/index/retrieving system are converted into data for another different system (step 475, FIG. 7) from the group of image reporting/archiving systems and the data storage/index/retrieving system (exemplary embodiments of conversions of data are disclosed hereinbelow) and data from/to the data storage/index/retrieving system is received/transmitted to/from a system for converting data (step 470, FIG. 7). (Data as used herein includes metadata.)

In order to further illustrate the present teachings, an exemplary embodiment is disclosed hereinbelow.

Figure 1:
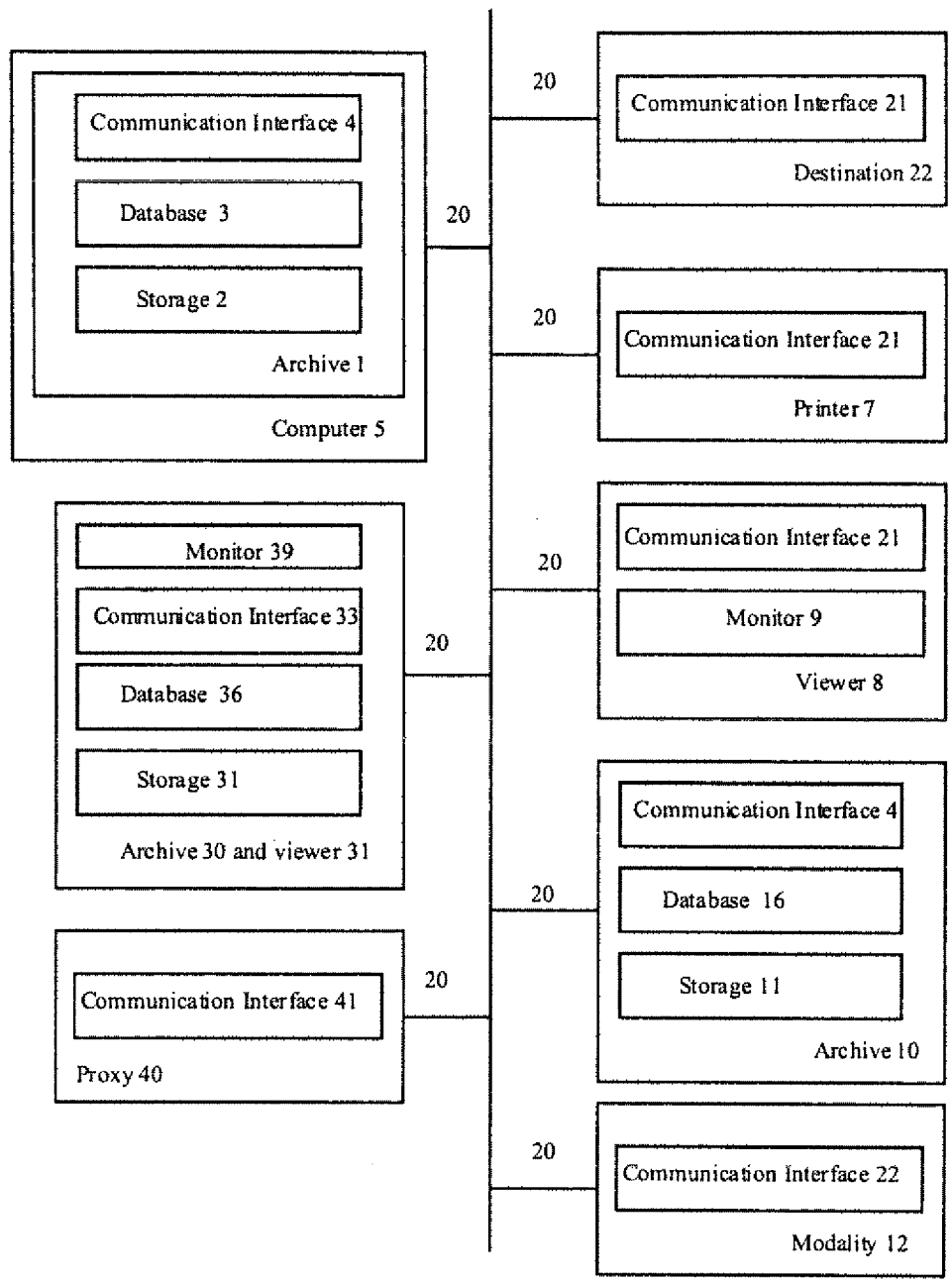
FIG. 1 is a schematic block diagram representation of a picture archiving and communication system architecture including an embodiment of the system of these teachings.

FIG. 1 illustrates the architecture for a PACS system to which the system described by these teachings can be connected. The expression "Proxy" will be used to designate an exemplary embodiment of the system of these teachings. The PACS system of FIG. 1 is for descriptive purpose only and should not be considered a limitation of these teachings.

The PACS system includes an archive 1, which may include a mass storage 2, a database 3, a communication interface 4, and a computer 5. The mass storage 2 may be provided, for example, by any combination of hard disks, CD-ROMs and/or tapes. The mass storage 2 is used for the storage of the imaging information objects. The database 3 is any commercial or non commercial database software, configured with tables, and capable of providing the function of accessing the imaging information object's data from a combination of attributes describing that imaging information object. The communication interface 4 is, generally, a software whose function is to exchange, with a standard communication protocol, the imaging information object or attributes about the imaging information objects between the archive 1 and communication peers. The computer 5 is to run the software necessary to control the mass storage 2, the database 3 and the communication interface 4. The archive 1 is connected to the network through the network connection 20. Communication peers are connected to the network through network connection 20. Communication peers include consumers of imaging information objects such as a printer 7 that may print the imaging information object on papers or films, a viewer 8 that may include a monitor 9 to display the imaging information object, or another archive 10 which may store the imaging information object on its mass storage 11. Communication peers also includes producers of the imaging information objects, such as a medical imaging modality 12, or any medical acquisition system. It should be noted the art that other communication peers may be connected to network through network connection 20 and communication interface 21. It should also be noted that the communication interface 4, the database 3 and the mass storage 2 can be controlled by more than one computer as long as they altogether behave as one archive while communicating with peers, and that more than one imaging information object consumers, such as an archive 30 and a viewer 31, can be hosted by one computer with one or more communication interface 39. Proxy 40 is connected to the network through network connection 20 and communicates with archive 1 and archive 10 through the communication interface 41.

Figure 2:
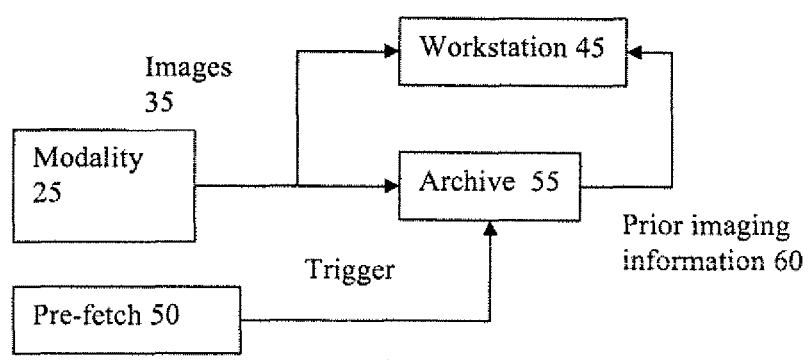
FIG. 2 is a schematic block diagram representation of an imaging flow in a conventional PACS.

FIG. 2 illustrates conventional imaging flow in a PACS systems. The images 1 are acquired by modalities 2, digitized if necessary, and communicated through the communication interface to the archive 3. Images 1 are forwarded or sent directly to one or multiple visualization stations 4, according to a pre-configured image flow. The visualization station receives the images and stores them on a local short-term storage media. A "pre-fetch" software 5 triggers the transfer of scheduled patients' prior imaging information 6 from the archive 3 to one or multiple visualization stations 4 according to a pre-configured image flow. In a possible architecture, the pre-fetch system is notified about the newly received imaging information in order to trigger the transfer of priors to workstations. Such notification can take place in various ways including combining the pre-fetch system with the archive. In another possible architecture, the pre-fetch system uses notifications about the scheduled acquisitions for patients to trigger the transfer of priors to workstations. Such notifications can be achieved via network messages that are received by the pre-fetch system from the scheduling application. Of importance here are the prior information objects that are available with newly generated information objects for interpretation on the workstation. Also of importance are the prior information objects that are available from the archive upon a consumer's request. In reference to FIG. 1., a user on the workstation can query the archive using the communication interface 4 and the network connection 20 about imaging information objects that match specific query parameters such as belonging to a specific patient. Likewise, the user on the workstation can access using the communication interface 4 and the network connection 20 and can visualize on the workstation imaging information objects that are retrieved from the archive. Accessing and visualizing current and prior information objects are necessary for providing quality of care.

Figure 3:
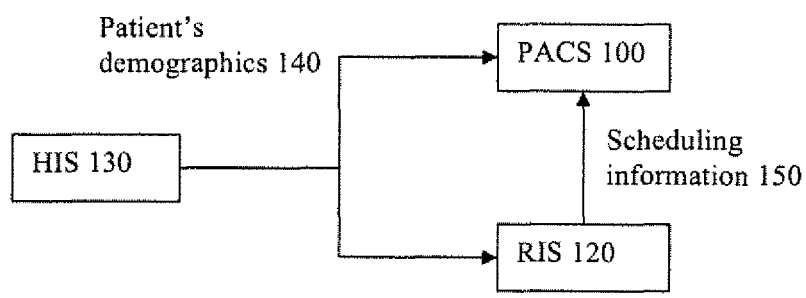
FIG. 3 is a schematic block diagram representation of information systems utilize in a conventional imaging service process.

FIG. 3 illustrates conventional information systems that are involved in an imaging service process. PACS 1 is responsible of managing the imaging service process that results in generation of images and other related imaging information. A radiology information system 2 is usually responsible for scheduling imaging acquisitions and interpretations. A Hospital Information System 3 (HIS) is responsible for registering patients and providing patients' demographics. Patient demographic information 4 is communicated from the HIS to RIS and PACS through a communication interfaces and network connection. Scheduling information 5 is communicated from the RIS to the PACS through communication interfaces and network connection. Of importance here is the patient identification that is managed by the HIS and shared with other information systems involved in the imaging process. In the absence of the communication interfaces and network connection between the HIS and other systems, patient's identification is entered manually at the various systems in a consistent way. The output of the imaging process is the diagnostic report that records the imaging information interpretation. The generation of the imaging report follows a workflow that may be managed by the RIS or the PACS. Of importance here is that the generated report is an important piece of the patient's history and thus needed during future imaging interpretation. In most imaging departments, the report workflow management and the report archiving are ensured by the RIS in which case the report management and archiving system—the RIS—is different from the image management system—the PACS. The link between the images and the report that belong to the same imaging process is diagnostically important. This is usually ensured by transmitting the order and scheduling information from the RIS to the PACS through communication interfaces and network connection. In the absence of the communication interfaces and network connection between the RIS and the PACS, the identification that links the images to the report is manually ensured. It is also possible to have the PACS manages the report workflow and report archiving along with the images and other imaging information.

Figure 4:
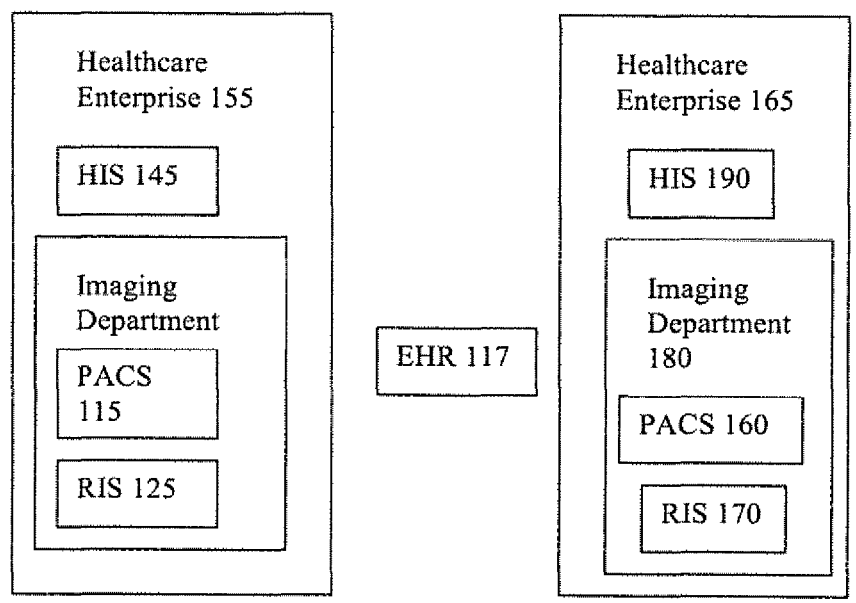
FIG. 4 is a schematic block diagram representation of multiple conventional enterprises involved in a patient's care.

FIG. 4 illustrates multiple conventional enterprises that are involved in the patient care. PACS 1 and RIS 2 belong to imaging department 3. Imaging department 3 and HIS 4 belong to healthcare enterprise 5. Likewise, PACS 6 and RIS 7 belong to imaging department 8. Imaging department 8 and HIS 9 belong to healthcare enterprise 10. It should be noted that exemplary enterprises shown should not be considered as a limitation as other enterprises are also involved in the patient's care. Is should also be noted that although one architecture is depicted in FIG. 4, other architectures are within the scope of these teachings. The different imaging departments may fulfill different imaging processes, manage the archiving of imaging information for possibly the same patient, and may uses dissimilar patient's identification. The information communication may occur between systems belonging to the same enterprise over communication network with limited security. If communication with outside the enterprise is not possible, limited security within the enterprise may be sufficient as the environment is considered a trusted one. Therefore, within an imaging department, communication usually occurs on a trusted network with almost no security other than access authorization to systems via user names and passwords. FIG. 4 also depicts an EHR system 11. It should be noted that the system shown may in fact be composed of multiple systems cooperating together to fulfill the functionality of the EHR system pertinent to these teachings, that is answering query and retrieve requests for clinical information that match specific parameters such as belonging to a specific patient. Of importance here is the communication protocol used by the EHR to communicate information that may be different from the communication protocol used by the PACS or the RIS to communicate imaging information objects. Also of importance here is the patient identification that may different between the various enterprises. Of importance as well is the security level that is different when communication within the same enterprise or within the same imaging department from the security level needed to communicate information outside of the imaging department.

Figure 8:
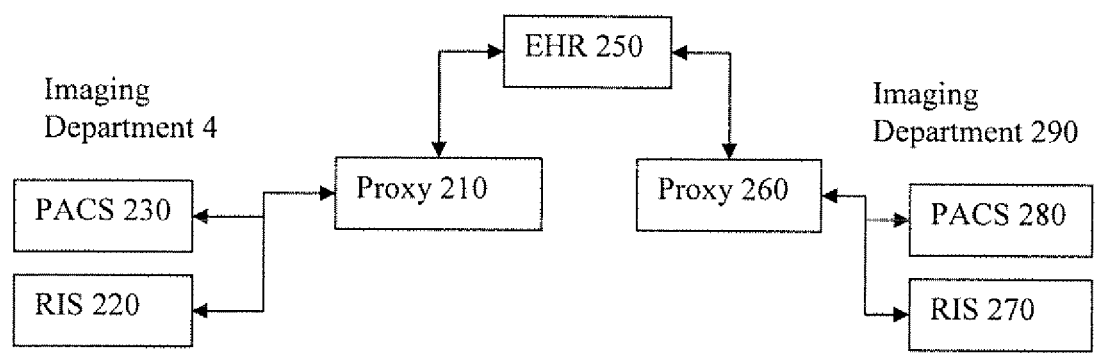
FIG. 8 is a schematic block diagram representation of an exemplary embodiment of the network architecture of these teachings.

FIG. 8 illustrates one embodiment of a network architecture of these teachings where one embodiment of the system of these teachings, Proxy 210, communicates with the RIS 220 and the PACS 230 from an imaging department 240 and with the EHR 250 and where another embodiment of the system of these teachings, Proxy 260, communicates with the RIS 270 and the PACS 280 from an imaging department 290 with the EHR 250. In the embodiment of the system of these teachings ensure bi-directionally coupling of the imaging department to the EHR, wherein the PACS, the RIS and the EHR operate with different communication protocols, and/or different security, and/or use different patient identification.

Exemplary embodiments of systems and methods are disclosed for bi-directionally coupling a Picture Archiving and Communication System (PACS) and an imaging reporting system from one side to the Electronic Health Record (EHR) in another side, wherein the PACS, the reporting and the EHR operate with different communication protocols, different security requirements, and use different patient identification. In one embodiment of these teachings, the PACS system uses the Digital Image and Communication (DICOM) protocol to encode and communicate images and related information. The EHR system may be any other type of system having at least one characteristic that precludes direct communication between the PACS and the EHR. In an exemplary embodiment the EHR uses ebXML encoded information over the SOAP communication protocol, and furthermore uses a different patient identification. A protocol conversion system that includes information processing method is positioned for receiving a communication from the PACS or the reporting system and converting the transmission into a transmission that is suitable for transmission into the EHR system, or for receiving a transmission from the EHR system and converting the transmission into a transmission that is suitable for transmission into the PACS or the reporting system.

In one embodiment, the present teachings provide a system and a method for bi-directionally coupling a Picture Archiving and Communication System (PACS) and/or an imaging reporting system to the Electronic Health Record (EHR), wherein the PACS, the imaging reporting system and the EHR operate with different communication protocols, different security requirements, and use different patient identification.

In an embodiment of these teachings, the PACS system uses the Digital Image and Communication (DICOM) protocol to encode and communicate images and related information. The EHR system may be any other type of system having at least one characteristic that precludes direct communication between the PACS and the EHR. In an exemplary embodiment the EHR uses ebXML encoded information over the SOAP communication protocol, and furthermore uses a different patient identification.

In accordance with one aspect of these teachings, a hybrid communication system is formed by placing a protocol converter between the PACS and the EHR, two systems that communicate with dissimilar communication protocols, thereby linking these two dissimilar communication systems for bi-directional imaging and other clinical information communications.

In accordance with another aspect of these teachings, the patient's identification and patient's demographics encoded within the information object are re-conciliated with the patient's identification and patient's demographics known to the PACS and/or reporting system when those information objects are imported from outside the imaging department to the PACS and/or reporting system.

In accordance with still another aspect of these teachings, the security level and/or security algorithms applied when communicating with one communication protocol can be different from the security level and/or security algorithms applied when communicating with the other communication protocol. For example, the communication protocol used to communicate with the EHR can use data encryption and system authentication while communicating with the PACS can be performed with a protocol with no security requirements.

In accordance with yet another aspect of these teachings, a query transaction from the PACS is transformed into a query to the EHR. To that end, the patient's identification of the PACS is mapped to the patient's identification of the EHR. Also, a query response from the EHR is transformed into a query response to the PACS. To construct the query response to the PACS, the query response of the EHR is processed and additional communication transactions to the EHR may be performed. Moreover, references to non-DICOM information objects are included in the query response as if these information objects were DICOM information objects.

In accordance with a further aspect of these teachings, information objects can be retrieved from the EHR or other systems located outside of the imaging department and forwarded to the PACS or the reporting system located within the imaging department. To that end, the patient's identification encoded in the information object is re-conciliated with the patient's identification used within the imaging department and the encoding of the information object is transformed to an encoding that is acceptable to the receiving system.

In accordance with still another aspect of these teachings, imaging information generated during imaging service processes within the imaging department can be made available for access through the EHR. To that end, information to be published to the EHR is constructed, according to the EHR encoding rules and formats, from the imaging information. Metadata describing published information, which can be used by the EHR to index the available published information, is also constructed from that information. Furthermore, the patient's identification that is encoded in the imaging information is transformed into another patient's identification suitable for the EHR before it is included in the metadata.

One embodiment of these teachings can provide a user with administration privileges a mean of controlling the imaging information to publish by specifying the type of information suitable for publication One embodiment of these teachings can keep trace of all published information for management and maintenance purposes such as managing replacement of, or addition to, previously published information.

In accordance with still another aspect of these teachings, relationships between imaging information that exist in the imaging department information model are maintained after publication. Examples include the relationship between a report and a set of images where the report is the result of the images interpretation.

In accordance with still another aspect of these teachings, relationships between information objects that should exist in the EHR domain are ensured. Some of these relationships do not necessarily exist in the imaging department domain as some information objects do not exist in the imaging department domain but are constructed for the sole purpose of publication by transformation of existing information. Other relationships may exist in the imaging department domain between 2 or multiple imaging information objects; however, the relationship encoding is transformed into another relationship encoding suitable for the EHR.

One embodiment of these teachings can provide access to information objects that are published to the EHR but kept persistent within the imaging department. To provide access from outside the department to information objects inside the department, communication protocol conversion, different security constraints and information processing or information transformation are applied.

One embodiment of these teachings can provide logical grouping when publishing information objects.

One embodiment of these teachings can provide a method for publishing all imaging information objects that were persistent in the imaging department prior to establishing the connection to the EHR.

In one embodiment if these teachings the PACS communicates with the DICOM protocol, the RIS communicates by exchanging Health Level 7 messages and the EHR communicates according to the Integrating Healthcare Enterprise Cross-Enterprise Document Sharing for Imaging Integration profile (XDS-I) that consists in exchanging with the SOAP communication protocol messages that are encoded according to the ebXML standard.

Figure 9:
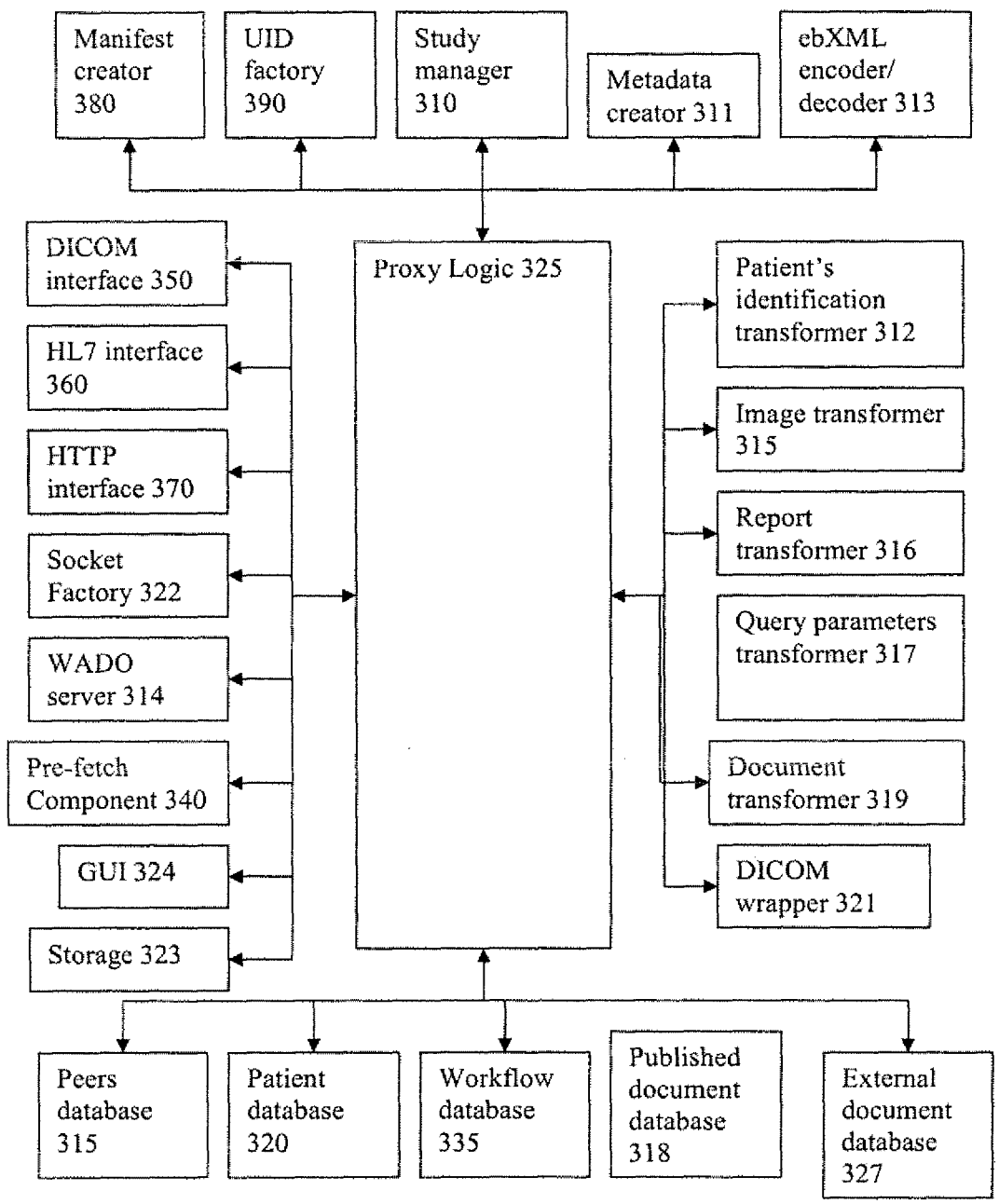
FIG. 9 is a schematic block diagram representation of an exemplary embodiment of the system described by these teachings.

FIG. 9 illustrates a block diagram of an embodiment of the system of these teachings, hereinafter referred to as "Proxy," where the embodiment comprises a database 315 for communication peers to store for each communication peer its complete address along with its communication and security parameters; patient database 320 to store patients' demographics and identification; workflow database 335 to store transient order and procedure information, pre-fetch component 340 that triggers a pre-fetch event to query and retrieve EHR information for a specific patient according to scheduled procedure information and pre-fetch internal logic; DICOM interface 350 to send and receive DICOM communication; Health Level 7 (HL7) interface 360 to send and receive HL7 message; HTTP/SOAP interface 370 to send and receive HTTP and SOAP encoded messages; manifest creator 380 that creates a manifest from instance UIDs; UID factory 390 to creates UIDs; study manager 310 that decides whether a specific study is complete according to scheduled procedure information, received instances and report and internal logic; metadata creator 311 that creates the metadata from database and instances information; patient's identification transformer 312 that transforms the local patient's identification to the EHR patient's identification or transforms the EHR patient's identification to the local patient's identification by querying a cross-referencing patient's identification or by applying specific rules; ebXML encoder and decoder 313; DICOM WADO server 314 to accept and respond to WADO (Web Access to DICOM Persistent Objects) requests; image transformer 315 that transforms a DICOM image to JPEG or MPEG; report transformer 316 that transforms a DICOM Structured Report (SR) to a PDF, text or HL7 Clinical Document Architecture (CDA) format and transforms an HL7 report to a PDF, text or CDA format; query parameters transformer 317 that transforms DICOM query parameters into ebXML query parameters; published document database 18 to index and stores published documents; external Document database 327 to store the external DICOM and non-DICOM instances parameters and location; document transformer 319 to transform a CDA encoded document into text, JEPG or PDF; DICOM wrapper 321 to wrap a JPEG image into a secondary capture DICOM instance or a PDF document into a PDF encapsulated DICOM instance; socket factory 322 to create a TCP socket according to security parameters of the communication peer; mass storage 323; graphical user interface 324 to visualize information from the database and to input user's actions; and "Proxy" logic 325 that coordinates all other components and apply the logic needed to couple the imaging department to the EHR.

The exemplary embodiment of the system of these teachings, hereinafter "Proxy," publishes information generated by the imaging department to the EHR, in which case the exemplary embodiment, "Proxy," is the source of the information with respect to the EHR. Information generated by the imaging department can be images or other information objects. Images are usually encoded and communicated with the DICOM standard and communication protocol.

Imaging reports may be encoded and communicated with DICOM. Alternatively, imaging reports may be communicated be exchanging HL7 messages. Related information objects are usually encoded and communicated with DICOM. Examples of related information objects include DICOM Presentation States, DICOM Key Object Selection or any other DICOM encoded object.

To publish a set of images, the exemplary embodiment, "Proxy," is informed about the set of images to be published, constructs a document referencing the set of images in a format acceptable for the EHR, constructs the metadata that is needed by the EHR to describe the set of images, determines the patient's identification used by the EHR, and submits the constructed document alone or with the report that is the interpretation result of these images. Furthermore, the exemplary embodiment, "Proxy," saves the constructed manifest and answers requests for retrieving published images and other instances.

To publish a set of images, the exemplary embodiment, "Proxy," determines the instances to publish and constructs a DICOM manifest. The DICOM manifest references all instances of images or other DICOM objects that are to be published. The manifest also references the DICOM address known as the Application Entity where the images can be retrieved. The Application Entity can be fixed and taken from pre-configuration information without any loss of generality. One exemplary embodiment is described with an application entity that designate Proxy itself in which case, Proxy is required to answer retrieve requests from consumers.

To construct the manifest, the exemplary embodiment, "Proxy," needs the study instance UID, the series instance UID and the instance UID of every instance to be referenced by the manifest. To get these UID's three embodiments are described. In the first embodiment, the exemplary embodiment of the system of these teachings, "Proxy," receives all DICOM instances generated during an imaging process by receiving a DICOM C-Store from a system within the imaging department, such as from the PACS, the exemplary embodiment, "Proxy," extracts the needed UID's and constructs the manifest. To construct the manifest, the exemplary embodiment, "Proxy," applies a set of rules in order to discard instances of specific types by not referencing them in the manifest. A rule is based on the instance class UID and on specific instance information capable of further characterizing specific information object types such as a code describing the information object title. An example consists in not publishing DICOM Key Object Selection instance whose title indicates that it was generated for quality control purposes. The published manifest is archived by the exemplary embodiment, "Proxy," and is indexed in its database so that Proxy knows what was published and the time of publication. In the second embodiment of these teachings, the exemplary embodiment, "Proxy," queries the PACS for instances generated during a specific time period, the last day for example, the exemplary embodiment, "Proxy," can query at fixed time interval. For example, the exemplary embodiment, "Proxy," can query at mid-night for all instances generated the day before in order to publish them. In the third embodiment of these teachings, Proxy receives notifications of availability of instances by mean of a DICOM service. The three embodiments just described illustrate how Proxy knows about the instances to publish. However, ideally Proxy needs to publish instances from a complete study otherwise a manifest replacement may be needed. In order to know when a study is complete, Proxy applies some logic. One instance consists in deciding that a study is complete if the Proxy has the verified report. In a another instance, the exemplary embodiment, "Proxy," knows what instances to expect by receiving order and scheduling information with an HL7 message and also from pre-configured information that describes the minimum number of instances of specific types that are generated to fulfill a specific imaging procedure, the exemplary embodiment, "Proxy," can also delay the publication for a certain time to increase the probability that all expected instances have been generated and that their UIDs are known.

Metadata that describes an imaging document to be published such as a set of images or a report is constructed from various information fields or sources according to mapping rules specific to the exemplary embodiment, "Proxy." The exemplary embodiment, "Proxy," has, in its database, information about the patient's demographics and about the performed imaging procedure. This database information is either extracted from patient's registration and procedure messages received by the exemplary embodiment, "Proxy," or extracted from received clinical documents such as the DICOM images or the report. To construct the metadata, patient and procedure information is transformed and encoded according to an encoding format acceptable to the receiving system. Metadata that do not relate to patient or procedure information such as the originating institution is constructed according to rules, from pre-configured information specified to the exemplary embodiment, "Proxy."

The exemplary embodiment, "Proxy," transforms the Patient Identification from a local healthcare enterprise patient identification to the EHR patient identification, before communicating with a system part of the EHR for publishing a document of for information query.

Two embodiments for mapping the patient's identification are described hereinafter. In the first embodiment, an external system capable for mapping the local patient identification used within a specific healthcare enterprise to the patient's identification needed by the EHR is available for answering a query request over a communication network. In this case, the exemplary embodiment, "Proxy," issues a query request to that system by including in its query request the local healthcare enterprise patient's identification and by querying for the EHR patient's identification. Conversely, the exemplary embodiment, "Proxy," issues a query request to that system by including in its query request the EHR patient's identification and by querying for the local healthcare enterprise patient's identification. In one instance, the exchanged message is encoded in conformance to the HL7 standard. In the second embodiment of these teachings, Proxy constructs the patient's identification needed by the EHR by applying a rule to specific patient's information. An example includes generating the EHR patient's identification from an identification issued by an external organization according to a rule shared by all cooperating systems such as appending the birth date to the a healthcare number issued by a governmental organization. Conversely, the local healthcare enterprise patient's identification is mapped from the EHR patient's identification by parsing and extracting the various part of the EHR patient's identification and mapping them to the local patient's identification from the Proxy database. The information needed to construct the EHR patient's identification, such as a healthcare number, may not be present from the DICOM instances or other documents to publish. Therefore, Proxy receives patient's information and demographics and stores it in its database. In this embodiment, Proxy receives an HL7 message over the communication network, when the patient is registered and when the patient's information is corrected.

Acting as the source of information, Proxy also enables external systems to retrieve published information objects. In one embodiment of these teachings, Proxy responds to DICOM Query, DICOM Retrieve and DICOM WADO Requests.

The exemplary embodiment, "Proxy," receives DICOM Retrieve requests from systems outside the imaging department. In order to respond to such request, Proxy issues a DICOM retrieve request to the PACS inside the imaging department for requesting the instances that are requested by the external system, receives with a DICOM C-store the instances requested from the PACS, and issues a DICOM C-store on the external requesting system to store the received instances.

The exemplary embodiment, "Proxy," receives DICOM WADO requests from systems outside the imaging department. Such request uses the HTTP protocol. In order to respond to such request, Proxy issues a DICOM retrieve request to the PACS inside the imaging department for requesting the instances that are requested by the external system, receives with a DICOM C-store the instances requested from the PACS. Depending on the WADO request, the exemplary embodiment, "Proxy," needs to transform the received instance either into a DICOM part 10 format or into a different format such as transforming a DICOM image into a JPEG image or transforming a DICOM structured report into a PDF document, the exemplary embodiment, "Proxy," includes the transformed instance in its HTTP response to the external requesting system.

To publish the imaging report, the exemplary embodiment, "Proxy," receives the imaging report from a system within the imaging department, transforms the encoding of the report content into a format acceptable for the EHR, constructs the metadata that is needed by the EHR to describe the report, determines the patient's identification used by the EHR, and submits the report document either with the images and instances that were interpreted to generate it or with a reference to those images and instances if they are already published.

The exemplary embodiment, "Proxy," receives the imaging report encoded in a specific format, over the communication network using a specific communication protocol, from a system within the imaging department. Two embodiments are described. The description of only these two embodiments should not be considered as a limitation to these teachings. In the first embodiment, the report is encoded as a DICOM structured report and is received by Proxy using the DICOM communication protocol by means of a DICOM C-Store message. In the second embodiment, the report is encoded as an HL7 message and is received by Proxy with an unsolicited transmission of an HL7 observation message or an observational report.

The exemplary embodiment, "Proxy," transforms the encoding of the report into a format acceptable to the EHR. Many embodiments exist and these teachings are not limited to any specific embodiment. Of importance here is that a content transformation module is needed and that subsequent steps deal with the output document of this transformation independently of its format. One example of such transformation includes transforming the DICOM SR into an HL7 CDA document or into plain text.

The exemplary embodiment, "Proxy," constructs the metadata that is needed by the EHR to describe the report, according to the same method used to construct the metadata for the manifest.

The exemplary embodiment, "Proxy," links the report to the set of images and other instances that were used to generate it. Two different embodiments are described. In the first embodiment, the report received by Proxy is a DICOM SR, bears the same study instance UID as the images and contains in its header the list of current and prior instances that were interpreted to generate it. In this embodiment the report and the images have the same study instance UID. In the second embodiment, the report received by Proxy is not a DICOM instance and therefore, does not bear a study instance UID. In this embodiment, a different identification common to the images and to the report is used to link them. Such identification is usually, but not limited to, the accession number.

The exemplary embodiment, "Proxy," submits the manifest that references the set of images and/or the report to an external system known as the Document Repository. The role of such system is specified in the IHE ITI technical framework. The communication protocol used to submit the manifest is also described in the IHE ITI technical framework. This communication protocol uses a message encoded according to ebXML over HTTP. Two embodiments are described. In the first embodiment, the manifest and the report are submitted together in a single submission set. In the second embodiment the manifest and the report are submitted separately in different submission sets.

The exemplary embodiment, "Proxy," submits the manifest and the report together in a single submission set. Therefore, Proxy waits until the manifest and the report that is linked to the image set referenced within the manifest are ready for publishing and submits them together. Proxy saves in its database the published documents along with their unique identifications. A document unique identifier can be generated by the exemplary embodiment, "Proxy," or can be left blank by Proxy according to a deployment decision. When a document unique identifier is not generated by Proxy, the exemplary embodiment, "Proxy," issues a query to the Registry to receive it.

Even though submitting the manifest and the report together in a single submission set is preferable, there are cases where submitting the manifest without any extra delay waiting for the report to become ready is necessary, the exemplary embodiment, "Proxy," submits the manifest without the report and saves its unique identifier. In the case where the unique identifier is not generated by Proxy, Proxy issues a query to the registry to receive it. Subsequently, the exemplary embodiment, "Proxy," submits the report that is linked to the image set referenced within the previously published by referencing the previously published manifest from within the submission set.

In the instance where the received report should replace a previously published report, Proxy issues a replacement request to the EHR with the new report and a reference to the old one. By decoding the received report, the exemplary embodiment, "Proxy," determines whether it is a replacement such as an amendment or not. From its internal database, Proxy knows whether the previous report has been published or not. If the received report is a replacement and the previous report has been published, Proxy issues the replacement to the ER.

The exemplary embodiment, "Proxy," enables the PACS to retrieve DICOM and non-DICOM information objects that are published to the EHR, in which case the exemplary embodiment, "Proxy," is the consumer of published information with respect to the EHR. The exemplary embodiment, "Proxy," also enables the RIS to receive imaging reports that are published to the EHR in which case Proxy is the consumer of published imaging report with respect to the EHR.

The exemplary embodiment, "Proxy," receives a DICOM Query from the PACS and responds to that query. Proxy receives a DICOM Query request for a specific patient, extracts the DICOM query parameters, maps the DICOM query parameters into parameters acceptable to the EHR, determines the patient's identification used by the EHR, issues a query to the EHR registry using the EHR communication protocol, receives the registry query response where each match includes a reference to a published document or a published manifest, retrieves all referenced manifests using the EHR communication protocol, decodes the manifests, stores in its database of external documents the information found in the manifests, stores in its database of external documents the information about non-DICOM information objects, constructs the DICOM query response and answers the DICOM query.

The exemplary embodiment, "Proxy," issues a Query request to the EHR to query for information for a specific patient in response to a trigger from its internal pre-fetch component or to a manual trigger. The exemplary embodiment, "Proxy," determines the patient's identification used by the EHR, issues a query to the EHR registry using the EHR communication protocol, receives the registry query response where each match includes a reference to a published document or a published manifest, retrieves all referenced manifests using the EHR communication protocol, decodes the manifests, stores in its database of external documents the information found in the manifests, and stores in its database of external documents the information about non-DICOM information objects.

The exemplary embodiment, "Proxy," stores in its database of external documents the information found in the retrieved manifests such as the Study UID, the Series UID, the instance UID, the Application Entity in addition to the EHR patient's identification and the local patient's identification.

The exemplary embodiment, "Proxy," stores in its database of external documents the non DICOM information such as the non DICOM document unique identifier, its type, its location, its DICOM UIDs if wrapped in a DICOM instance, in addition to the EHR patient's identification and the local patient's identification.

The exemplary embodiment, "Proxy," constructs the DICOM Query Response by including the UIDs found in the retrieved manifests. Additionally, Proxy includes references to non-DICOM objects in the query response as if they were DICOM objects. Decision to include references to non-DICOM objects or not is made according to a pre-configured policy.

The exemplary embodiment, "Proxy," issues a Retrieve request to an external system for retrieving information objects to answer a retrieve request that it receives from a system within the imaging department, or in response to a trigger from its internal pre-fetch component or in response to a manual trigger.

The exemplary embodiment, "Proxy," transforms the encoding of a non-DICOM information object that is retrieved from an external system into a DICOM encoding before storing the transformed information object onto a DICOM peer within the imaging department.

The exemplary embodiment, "Proxy," transforms the encoding of a non-DICOM information object or an imaging report that is retrieved from an external system into plain text before storing the transformed information object onto an HL7 peer within the imaging department.

Information objects retrieved from an external system in response to a pre-fetch trigger are sent to communication peers within the imaging department using a communication protocol and an encoding acceptable to that peer.

Information objects retrieved from an external system in response to a manual trigger are managed by Proxy and stored on its mass storage. Information objects managed by Proxy can be manually sent to communication peers within the imaging department using a communication protocol and an encoding acceptable to that peer.

When sending an information object to a communication peer, Proxy determines from its internal information the information object encodings and the communication protocol acceptable for that peer, The exemplary embodiment, "Proxy," transforms if needed, the information object into an encoding acceptable to that peer. Proxy uses a communication protocol acceptable to that peer to send the information object encoded in a format acceptable to that peer.

The exemplary embodiment, "Proxy," receives a DICOM Retrieve request from the PACS and responds to it. Proxy receives a DICOM Retrieve request for specific instances that were referenced in a previous DICOM query response, retrieves and receives the instances, changes the patient's identification encoded within the received instances to the patient's identification known inside the imaging department, issues a DICOM C-Store with those instance on the requestor, and answer the DICOM retrieve request with the adequate response.

To retrieve specific instances, the exemplary embodiment, "Proxy," finds from its database of external documents the external system identification where to retrieve those instances, finds from its configuration the communication protocol to use in communicating with the external repository system along with the information needed to construct its complete communication address, issues one or multiple retrieve requests to the external system, and receives the requested instances. (The embodiment described herein above is exemplary of the use of means for defining communication endpoints.)

The exemplary embodiment, "Proxy," issues a Retrieve request to an external system for retrieving information objects in response to a trigger from its internal pre-fetch component. Such a retrieve request is preceded by a query request to the registry for published information objects for a specific patient. Proxy retrieves and receives specific instances referenced in the previous query, changes the patient's identification encoded within the received instances to the patient's identification known inside the imaging department, and sends those instances to receiving systems within the imaging department. Proxy determines the receiving systems of a specific instance according to pre-configured information that encodes for each type of information object the list of destination peers.

The exemplary embodiment, "Proxy," issues a Retrieve request to an external system for retrieving information objects in response to a manual trigger. Such a retrieve request is preceded by a query request to the registry for published information objects for a specific patient. Proxy retrieves and receives specific instances referenced in the previous query, changes the patient's identification encoded within the received instances to the patient's identification known inside the imaging department, and stores those instances on its mass storage.

The exemplary embodiment, "Proxy," issues one or multiple retrieve requests to an external system to fulfill a retrieve request that it receives from a system inside the imaging department, that is triggered by its pre-fetch component or that is manually requested. As an example, in order for Proxy to answer a retrieve request from the PACS to retrieve a complete published imaging study identified by its Study UID, Proxy finds from its database the instance UIDs for all instances that belong to the identified study, issues multiple WADO requests to retrieve all instances, one WADO request per instance to retrieve, and stores all retrieved instances on the PACS.

The exemplary embodiment, "Proxy," re-conciliates the patient's identification encoded inside the information object to the local patient's identification before storing that information object onto a system in the imaging department. To achieve this reconciliation, Proxy maps from its database the information object identification to the EHR patient's identification, and then Proxy transforms the EHR patient's identification into the local patient's identification.

The exemplary embodiment, "Proxy," transforms a non-DICOM information object into a DICOM instance. Proxy transforms the information object content into a format ready for display such as a PDF document or a JEPG image. Proxy creates either a secondary capture DICOM instance to wrap the JEPG image or an encapsulated PDF. Proxy creates the needed UIDs and maps the patient and study information from the information available from its database. Proxy encodes within the created DICOM instance the patient's identification known inside the imaging department, stores the newly created DICOM UIDs, the document external UID, and the EHR patient's identification in its database of external documents. Proxy encodes DICOM descriptions of the document, the Series description for example, by transforming the document type into a meaningful description. Mapping of document types into DICOM descriptions is pre-configured and internally stored by Proxy.

The exemplary embodiment, "Proxy," transforms a non-DICOM information object or an imaging report into plain text that is included in an unsolicited transmission of an HL7 observation message or an observational report to an HL7 peer within the imaging department. Proxy uses the patient's identification known inside the imaging department while exchanging this message.

The exemplary embodiment, "Proxy," exchanges certificates with communication peers for node authentication. Proxy uses encryption when exchanging information on the network.

Proxy communicates with peers using any communication protocol over a secure socket layer. Communication protocols include DICOM, HL7 and HTTP.

The exemplary embodiment, "Proxy," decides and controls the security level of a communication. Levels consist of no secure socket, secure socket involving node authentication, secure socket involving node authentication and encryption.

The exemplary embodiment, "Proxy," sets the security level of a communication for each communication peer independently. For each communication protocol, Proxy listens on different logical addresses, where communication with each logical address is achieved with a different security level. For each logical address is associated a list of peers from which Proxy accepts communications. Communication initiated, on a logical address, from a peer that is not on the list of that address is refused by Proxy. Proxy initiates a communication with a communication peer with the appropriate security level determined from information stored in its database.

The techniques described above may be implemented in one or more computer programs executing on a programmable computer including a processor, a storage medium readable by the processor (including, for example, volatile and non-volatile memory and/or storage elements), and, in some embodiments, also including at least one input device, and/or at least one output device. Program code may be applied to data entered using the input device (or user interface) to perform the functions described and to generate output information. The output information may be applied to one or more output devices.

Elements and components described herein may be further divided into additional components or joined together to form fewer components for performing the same functions.

Each computer program (computer readable code) may be implemented in any programming language, such as assembly language, machine language, a high-level procedural programming language, an object-oriented programming language, or a combination thereof. The programming language may be a compiled or interpreted programming language.

Each computer program may be implemented in a computer program product tangibly embodied in a computer-readable storage device for execution by a computer processor. Method steps of these teachings may be performed by a computer processor executing a program tangibly embodied on a computer-readable medium to perform functions of these teachings by operating on input and generating output.

Common forms of computer-readable (computer usable) media include, for example, a floppy disk, a flexible disk, hard disk, magnetic tape, or any other magnetic medium, a CDROM, any other optical medium, punched cards, paper tape, any other physical medium with patterns of holes or other patterns, a RAM, a PROM, and EPROM, a FLASH-EPROM, any other memory chip or cartridge. A carrier wave, such as electromagnetic radiation or electrical signals in a network, or any other medium from which a computer can read is a known equivalent of the computer usable media.

Although these teachings has been described with respect to various embodiments, it should be realized these teachings are also capable of a wide variety of further and other embodiments within the spirit and scope of the appended claims.

What is claimed is:

1. A system for enabling bi-directional data communication from an image archiving system and a data storage/index/retrieving system, the system comprising:
   an interface configured for receiving/sending data according to a first protocol, said first protocol being utilized for data communication from the image archiving system;
   another interface configured for receiving/sending data according to a second protocol, said second protocol being utilized for data communications from the data storage/index/retrieving system and being different from said first protocol; said data storage/index/retrieving system storing patients' health history/record and enabling querying, retrieving information for a patient and publishing a patient's health information;
   at least one data conversion subsystem configured for converting data from a format used by the image archiving system into data in a format utilized by the data storage/index/retrieving system;
   at least another data conversion subsystem that converts data from a format used by the data storage/index/retrieving system into data in a format utilized by utilized by the image archiving system;
at least one database configured for storing data received from data systems, said data systems including the image archiving system and the data storage/index/retrieving system;
means for receiving/transmitting data front/to the data storage/index/retrieving system;
means for receiving/transmitting data from/to the image archiving system;
means for retrieving, from said at least one database, data received from the image archiving system and the data storage/index/retrieving system;
means for converting data/data characteristics from one of the image archiving system and the data storage/index/retrieving system into data/data characteristics for a different one of the image archiving system and the data storage/index/retrieving system; and
one or more processors; said one or more processors operatively connected to said interface, said another interface, said at least one data conversion subsystem, said at least another data conversion subsystem, said at least one database and said means;
said interface, said another interface, said at least one data conversion subsystem, said at least another data conversion subsystem, said at least one database and said means enabling bi-directional communication between the image archiving system and the data storage/index/retrieving system wherein the image reporting/archiving systems and the data storage/index/retrieving system operate with different protocols or with different protocols, different security requirements or/and use different patient identification.

2. The system of claim 1 wherein said means for receiving/transmitting data from/to the data storage/index/retrieving system, said means for receiving/transmitting data from/to the image archiving system, said means for retrieving, from said at least one database, data received from the image archiving system and the data storage/index/retrieving system and said means for converting data/data characteristics from one of the image archiving system and the data storage/index/retrieving system into data/data characteristics for a different one of the image archiving system and the data storage/index/retrieving system comprise;
a non-transitory computer usable medium having computer readable code embodied there in, said computer readable code being configured for causing at least one processor to:
receive/transmit data from/to the data storage/index/retrieving system;
receive/transmit data from/to the image archiving system,
retrieve, from said at least one database, data received from the image archiving system and the data storage/index/retrieving system; and
convert data/data characteristics from one of the image archiving system and the data storage/index/retrieving system into data characteristics for a different one of the image archiving system and the data storage/index/retrieving system.

3. The system of claim 1 wherein said first protocol comprises a DICOM protocol.

4. The system of claim 1 wherein said first protocol comprises an HL7 protocol.

5. The system of claim 1 wherein said second protocol comprises a SOAP protocol.

6. A network comprising:
a group of image reporting/archiving systems comprising:
an image archiving system; said image archiving system receiving/transmitting image data according to a first protocol; and
an image information system; said image information system receiving/transmitting image information data according to a second protocol; said second protocol being different from said first protocol
a data storage/index/retrieving system; said data storage/index/retrieving system storing patients' health history/record and enabling querying, retrieving information for a patient and publishing a patient's health information; said data storage/index/retrieving system receiving/transmitting data according to a third protocol; said third protocol being different from said first protocol and said second protocol; and
a converting system comprising:
a first interface configured for receiving data according to said first protocol; said first interface enabling transmitting/receiving data to/from said image archiving system from/to said converting system;
a second interface configured for receiving data according to a second protocol; said second interface enabling transmitting/receiving data to/from said image information system from/to said converting system;
a third interface configured for receiving/transmitting data according to a third protocol; said third interface enabling transmitting/receiving data to/from said data storage/index/retrieving system from/to said converting system;
a first conversion subsystem configured for converting data from a format used by the image archiving system into data in a format utilized by the data storage/index/retrieving system;
a second conversion subsystem configured for converting data from a format used by the image information system into data in a format utilized by the data storage/index/retrieving system;
a third data conversion subsystem configured for converting data from a format used by the data storage/index/retrieving system into data in a format utilized by the image archiving system configured for converting data from a format utilized by the data storage/index/retrieving system into data in a format utilized by the image information system;
at least one database configured for storing data from data systems, said data systems including the image archiving system, the data storage/index/retrieving system and the image information system;
means for receiving/transmitting data from/to the data storage/index/retrieving system;
means for receiving/transmitting data from/to the image archiving system;
means for receiving/transmitting data from/to the image information system;
means for retrieving, from said at least one database, data received from the image archiving system, the data storage/index/retrieving system and the image information system; and
means for converting data/data characteristics from one system in the network into data for another system in the network, said another system having data requirements different from the data requirements of said one system;

said converting system enabling bi-directional communication between the group of image reporting/archiving systems and the data storage/index/retrieving system wherein the image reporting/archiving systems, the image information system and the data storage/index/retrieving system operate with different protocols or with different protocols, different security requirements or/and use different patient identification.

7. The network of claim 6 wherein said means for converting data/data characteristics comprise:
    means for converting data/data characteristics from the image archiving system into data/data characteristics for the data storage/index/retrieving system;
    means for converting data/data characteristics from the data storage/index/retrieving system into data/data characteristics for the image archiving system;
    means for converting data from the image information system into data for the data storage/index/retrieving system; and
    means for converting data from the data storage/index/retrieving system into data for the image information system.

8. The network of claim 6 wherein said converting system further comprises at least one processor; and
    wherein said means for receiving/transmitting data from/to the data storage/index/retrieving system, said means for receiving/transmitting data from/to the image archiving system, said means for receiving/transmitting data from/to the image information system, said means for retrieving, from said at least one database, data received from the image archiving system, the data storage/index/retrieving system and the image information system and said means for converting data/data characteristics comprise;
        a non-transitory computer usable medium having computer readable code embodied there in, said computer readable code causing at least one processor to:
            receive/transmit data from/to the data storage/index/retrieving system;
            receive/transmit data from/to the image archiving system;
            receive/transmit data from/to the image information system;
            retrieve, from said at least one database, data received from the image archiving system, the data storage/index/retrieving system and the image information system; and
            convert data/data characteristics a from said one system in the network into data/data characteristics for said another system in the network.

9. The network of claim 8 wherein said computer readable code, in causing at least one processor to convert data/data characteristics, causes at least one processor to:
    convert data/data characteristics a from the image archiving system into data/data characteristics for the data storage/index/retrieving system;
    convert data/data characteristics from the data storage/index/retrieving system into data/data characteristics for the image archiving system;
    convert data/data characteristics from the image information system into data/data characteristics for the data storage/index/retrieving system; and
    convert data/data characteristics from the data storage/index/retrieving system into data/data characteristics for the image information system.

10. The network of claim 6 wherein said first protocol comprises a DICOM protocol.

11. The network of claim 6 wherein said second protocol comprises an HL7 protocol.

12. The network of claim 6 wherein said third protocol comprises a SOAP protocol.

13. A method for bi-directionally communicating data between a group of image reporting/archiving systems and a data storage/index/retrieving system, the method comprising the steps of:
    receiving/transmitting data from/to the group of image reporting/archiving systems to/from a system for converting data;
    retrieving data from the group of image reporting/archiving systems and the data storage/index/retrieving system; said data storage/index/retrieving system storing patients' health history/record and enabling querying, retrieving information for a patient and publishing a patient's health information;
    converting data/data characteristics from one system from the group of image reporting/archiving systems and the data storage/index/retrieving system into data/data characteristics for another different system from the group of image reporting/archiving systems and the data storage/index/retrieving system; and
    receiving/transmitting data from/to the data storage/reporting system to/from the system for converting data;
    said receiving/transmitting data, said retrieving data, said converting data/data characteristics and said receiving/transmitting data from/to the data storage/reporting system enabling bi-directionally communicating data between a group of image reporting/archiving systems and a data storage/index/retrieving system wherein the image reporting/archiving systems and the data storage/index/retrieving system operate with different protocols or with different protocols, different security requirements or/and use different patient identification.

14. The method of claim 13 wherein the step of receiving/transmitting data from the group of image reporting/archiving systems comprises a step of receiving/transmitting data according to a DICOM protocol.

15. The method of claim 13 wherein the step of receiving/transmitting data from the group of image reporting/archiving systems comprises a step of receiving/transmitting data according to an HL7 protocol.

16. The method of claim 13 wherein the step of receiving/transmitting data from the data storage/index/retrieving system comprises a step of receiving/transmitting data according to a SOAP protocol.

17. The method of claim 13 wherein the step of converting data/data characteristics comprises the step of converting data format.

18. The method of claim 13 wherein the step of converting data/data characteristics includes the step of converting relationships between at least two data objects.

19. The method of claim 13 wherein the step of converting data/data characteristics comprises a step of converting patient identification and patient demographics.

20. The method of claim 13 wherein the step of converting data/data characteristics a comprises the step of converting references to data.

21. The method of claim 13 wherein the step of transmitting data to the storage/index/retrieve system comprises the steps of:
    determining a group of data for transmission; and
    transmitting said group of data.

22. A converter system for enabling bi-directional data communication from group of image reporting/archiving systems and a data storage/index/retrieving system, the converting system comprising:
- a first interface configured for receiving/transmitting data according to a DICOM protocol; said first interface enabling transmitting/receiving data to/from an image archiving system from/to the converting system; said image archiving system being one system from the group of image reporting/archiving systems and being a picture archiving and communication system (PACS);
- a second interface configured for receiving/transmitting data according to an HL7 protocol; said second interface enabling transmitting/receiving data to/from an image information system from/to the converting system, said image information system being another system from the group of image reporting/archiving systems;
- a third interface configured for receiving data according to a third protocol;
- said third interface enabling transmitting/receiving data to from said data storage/index/retrieving system from/to the converting system; said data storage/index/retrieving system storing patients' health history/record and enabling querying, retrieving information for a patient and publishing a patient's health information; said third protocol being different from DICOM and HL7;
- a first conversion subsystem configured for converting data from a format used by the PACS system into data in a format utilized by the data storage/index/retrieving system;
- a second conversion subsystem configured for converting data from a format used by the image information system into data in a format utilized by the data storage/index/retrieving system;
- a third data conversion subsystem configured for converting data from a format used by the data storage/index/retrieving system into data in a format utilized by the PACS system and converting data from a format utilized by the data storage/index/retrieving system into data in a format utilized by the image information system;
- at least one database of storing data from data systems, said data systems including the PACS system, the data storage/index/retrieving system and the image information system;
- means for receiving/transmitting data from/to the data storage/index/retrieving system;
- means for receiving/transmitting data from/to the PACS system;
- means for receiving/transmitting data from/to the image information system;
- means for retrieving, from said at least one database, data from the PACS system, the data storage/index/retrieving system and the image information system;
- means for converting data/data characteristics from a system from the group of the PACS system, the image information system and the data storage/index/retrieving system into data/data characteristics for a different system from the group of the PACS system, the image information system and the data storage/index/retrieving system; and
- one or more processors; said one or more processors operatively connected to at least one of said first, second and third interfaces, at least one of said first, second and third conversion subsystems, said at least one database and said means;
- said first, second and third interfaces, said first, second and third conversion subsystems, said at least one database and said means enabling bi-directional communication between the group of image reporting/archiving systems and the data storage/index/retrieving system wherein the image reporting/archiving systems and the data storage/index/retrieving system operate with different protocols or with different protocols, different security requirements or/and use different patient identification.

23. The system of claim 22 wherein said means for receiving/transmitting data from/to the data storage/index/retrieving system, said means for receiving/transmitting data from/to the PACS system, said means for receiving/transmitting data from/to the image information system, said means for retrieving, from said at least one database, data from the PACS system, the image information system and the data storage/index/retrieving system and said means for converting data/data characteristics from a system from the group of the PACS system, the image information system and the data storage/index/retrieving system into data/data characteristics for a different one of the PACS system, the image information system and the data storage/index/retrieving system comprise:
- a non-transitory computer usable medium having computer readable code embodied there in, said computer readable code cause at least one processor to:
  - receive/transmit data from/to the data storage/index/retrieving system;
  - receive/transmit data from/to the PACS system;
  - receive/transmit data from/to the image information system;
  - retrieve, from said at least one database, data for the PACS system the data storage/index/retrieving, system and the image information system; and
  - convert data/data characteristics from a system from the group of the PACS system, the image information system and the data storage/index/retrieving system into data/data characteristics for a different system from the group of the PACS system, the image information system and the data storage/index/retrieving system.

24. The converter system of claim 23 further comprising at least another non-transitory computer usable medium.

25. The converter system of claim 23 wherein said computer readable code further causes said at least one processor to construct metadata to be used by the data storage/index/retrieving system.

26. The converter system of claim 23 wherein said computer readable code further causes said at least one processor to generate an imaging report.

27. The converter system of claim 23 wherein said computer readable code further causes said at least one processor to transmit data to the storage/index/retrieving system causing the storage/index/retrieving system to replace/add to previously transmitted data.

28. The converter system of claim 23 wherein said computer readable code, in causing said at least one processor to transmit data to the data storage/index/retrieving system also applies rules to determine a group of data for transmission.

29. The converter system of claim 28 wherein said data for transmission comprises references to instances of objects.

30. The converter system of claim 22 further comprising means for converting and transmitting from the group of image reporting/archiving to the storage/index/retrieving system, data that existed in the group of image reporting/archiving before establishing the network connection between the group of image reporting/archiving and the storage/index/retrieving system.

31. The converter system of claim 22 further comprising means for defining communication endpoints, said communication endpoints comprising a name and a network address.

32. The system of claim 1 wherein the data/data characteristics comprise security requirements.

33. The system of claim 2 wherein the data/data characteristics comprise security requirements.

34. The network of claim 6 wherein the data/data characteristics comprise security requirements.

35. The network of claim 7 wherein the data/data characteristics comprise security requirements.

36. The network of claim 8 wherein the data/data characteristics comprise security requirements.

37. The method of claim 13 wherein the data/data characteristics comprise security requirements.

38. The method of claim 13 wherein the step of converting data/data characteristics includes the step of converting security requirements.

39. The converter system of claim 22 wherein the data/data characteristics comprise security requirements.

40. The converter system of claim 23 wherein the data/data characteristics comprise security requirements.

\* \* \* \* \*

UNITED STATES PATENT AND TRADEMARK OFFICE
CERTIFICATE OF CORRECTION

PATENT NO.       : 8,458,202 B2                                Page 1 of 1
APPLICATION NO.  : 12/300244
DATED            : June 4, 2013
INVENTOR(S)      : Rita Noumeir It is certified that error appears in the above-identified patent and that said Letters Patent is hereby corrected as shown below:

On the title page, under item (56) References Cited, and further under OTHER PUBLICATIONS, "JP Publication No. JP7320034(A), published Dec. 8, 2995" should read -- JP Publication No. JP7320034(A), published Dec. 8, 1995 --

In the Claims:

In Column 19, lines 1-2 (claim 1), "utilized by utilized by" should read -- utilized by --
In Column 19, lines 32-33 (claim 1), "with different protocols or with different protocols," should read -- with different protocols or --
In Column 19, line 45 (claim 2), "comprise;" should read comprise: --
In Column 20, line 9 (claim 6), "protocol" should read -- protocol; --
In Column 21, lines 6-7 (claim 6), "with different protocols or with different protocols," should read -- with different protocols or --
In Column 21, lines 35-36 (claim 8), "comprise;" should read -- comprise: --
In Column 21, line 50 (claim 8), "characteristics a from" should read -- characteristics from --
In Column 21, line 56 (claim 9), "characteristics a from" should read -- characteristics from --
In Column 22, lines 36-37 (claim 13), "with different protocols or with different protocols," should read -- with different protocols or --
In Column 22, line 61 (claim 20), "characteristics a comprises" should read -- characteristics comprises --
In Column 22, line 64 (claim 21), "storage/index/retrieve" should read -- storage/index/retrieving --
In Column 23, lines 20-21 (claim 22), "data to from" should read -- data to/from --
In Column 24, lines 5-6 (claim 22), "with different protocols or with different protocols," should read -- with different protocols or --
In Column 24, line 25 (claim 23), "code cause" should read -- code causes --
In Column 24, line 32 (claim 23), "PACS system the data storage/index/retrieving," should read -- PACS system, the data storage/index/retrieving --

Signed and Sealed this
Twenty-seventh Day of August, 2013

Teresa Stanek Rea
*Acting Director of the United States Patent and Trademark Office*